(12) United States Patent
Chen et al.

(10) Patent No.: US 9,187,773 B2
(45) Date of Patent: Nov. 17, 2015

(54) **METHOD FOR IMPROVING ACID TOLERANCE OF *PROPIONIBACTERIUM ACIDIPROPIONICI***

(71) Applicants: Jian Chen, Wuxi (CN); Guocheng Du, Wuxi (CN); Long Liu, Wuxi (CN); Jianghua Li, Wuxi (CN); Ningzi Guan, Wuxi (CN)

(72) Inventors: Jian Chen, Wuxi (CN); Guocheng Du, Wuxi (CN); Long Liu, Wuxi (CN); Jianghua Li, Wuxi (CN); Ningzi Guan, Wuxi (CN)

(73) Assignee: Jiangnan University, Wuxi, Jiangsu (CN)

( * ) Notice: Subject to any disclaimer, the term of this patent is extended or adjusted under 35 U.S.C. 154(b) by 67 days.

(21) Appl. No.: 14/047,968

(22) Filed: Oct. 7, 2013

(65) Prior Publication Data

US 2014/0178952 A1    Jun. 26, 2014

(30) Foreign Application Priority Data

Dec. 24, 2012 (CN) .......................... 2012 1 0566749

(51) Int. Cl.
*C12P 7/52* (2006.01)
(52) U.S. Cl.
CPC ........................................ *C12P 7/52* (2013.01)

(58) Field of Classification Search
None
See application file for complete search history.

(56) References Cited

PUBLICATIONS

Guan, N., Liu, L., Shin, H., Chen, R.R., Zhang, J., Li, J. Du, G., Shi, Z., and Chen, J., "Systems-level understanding of how Propionibacterium acidipropionici respond to propionic acid stress at the microenvironment levels: Mechanism and application", Journal of Biotechnology 2013, vol. 167, pp. 56-63.*
Senouci-Rezkallah, K., Schmitt, P., and Jobin, M.P., "Amino acids improve acid tolerance and internal pH maintenance in Bacillus cereus ATCC14579 strain", Food Microbiology 2011, vol. 28, pp. 364-372.*

* cited by examiner

*Primary Examiner* — Renee Claytor
*Assistant Examiner* — Michelle F Paguio Frising
(74) *Attorney, Agent, or Firm* — Lili Chen

(57) ABSTRACT

The invention provides a simple and effective method for improving acid tolerance of *P. acidipropionici* by adding arginine and/or aspartic acid to the culture medium. The acid tolerance of *P. acidipropionici* was improved by 60% and 20% respectively through adding arginine or aspartic acid into the culture medium. Consequently, PA production was improved by 36% and 26%, respectively. The maximal PA production was obtained by adding both 20 mM arginine and 20 mM aspartic acid. This method can be applied to large scale production of PA.

18 Claims, 2 Drawing Sheets

METHOD FOR IMPROVING ACID TOLERANCE OF *PROPIONIBACTERIUM ACIDIPROPIONICI*

CROSS-REFERENCES AND RELATED APPLICATIONS

This application claims the benefit of priority to Chinese Application No. 201210566749.3, entitled "A method for improving acid tolerance of *Propionibacterium acidipropionici* and applications thereof", filed Dec. 24, 2012, which is herein incorporated by reference in its entirety.

BACKGROUND OF THE INVENTION

1. Field of the Invention

The present invention relates to a method for improving acid tolerance and propionic acid productivity of *Propionibacterium acidipropionici*, and more particularly relates to a method of improving acid tolerance and propionic acid productivity of *P. acidipropionici* by adding arginine and aspartic acid during the cultivation of *P. acidipropionici*.

2. Description of the Related Art

The sustainable development of our society is severely hindered by energy shortages and environmental pollution. Using renewable biomass resources as raw materials for large-scale production of chemical products, medicine, food and agricultural materials is considered to be a promising way to resolve the current energy shortage and environmental crisis.

Propionic acid (PA) is an important mold inhibitor, and its calcium, sodium and potassium salts are widely used as food and feed preservatives. PA can also be used as a chemical intermediate for the synthesis of cellulose fibers, herbicides, perfumes, and pharmaceuticals. Currently, PA is mainly produced by petrochemical approaches. With the increasing concerns over environmental pollution and energy shortages, the microbial production of PA by propionibacteria receives ongoing interest and extensive studies have been done to improve PA yield. Microbial PA production is a typical product-inhibited process, and the accumulation of PA severely inhibits both cell growth and PA synthesis. To resolve this problem, NaOH or $Ca(OH)_2$ was added to maintain the pH at a stable level, which unfortunately will increase the osmotic pressure of fermentation broth and the costs of downstream extraction. Therefore, improving the acid tolerance of PA-producing microbes is an effective approach to increase microbial PA production. The present invention satisfies this need and provides other benefits.

DETAILED DESCRIPTION

The present invention provides a method for improving acid tolerance of *P. acidipropionici* by adding arginine and/or aspartic acid in the culture. The term "acid tolerance" as used herein refers to the concentration of an acid (e.g. PA), beyond which the proliferation and growth of a microbe (e.g. *P. acidipropionici*) is greatly inhibited.

The method comprises the following steps:

1. Method to Increase Acid Tolerance of *P. acdipropionici*

*P. acidipropionici* was first inoculated with sterile seed medium in anaerobic jars. The anaerobic jars were incubated at 30° C. for 60 h. To determine the effects of adding amino acids on acid tolerance of *P. acidipropionici*, the culture broth was transferred into anaerobic jars containing fresh seed medium with 2.5-5 g/L PA, 5-30 mM arginine and/or 5-30 mM aspartic acid added. The strains were then incubated at 30° C. for 40 h.

The *P. acidipropionici* was bought from China General Microbiological Culture Collection, and the strain code is CGMCC 1.2230.

The seed medium: 10 g/L yeast extract, 5 g/L tryptic soy broth, 1.5 g/L $KH_2PO_4$, 2.5 g/L $K_2HPO_4$, pH 7.0.

The method for improving acid tolerance of *P. acidipropionici* by adding amino acids can be achieved through the following methods:

adding 5-30 mM arginine into the seed medium;
adding 5-30 mM aspartic acid into the seed medium; or
adding both 5-30 mM arginine and 5-30 mM aspartic acid into the seed medium, among which the third method is preferred.

2. Methods to Increase PA Production

To determine the effects of adding amino acids on PA production of *P. acidipropionici*, *P. acidipropionici* was inoculated with sterile seed medium in anaerobic jars. The anaerobic jars were incubated at 30° C. for 60 h. The culture broth was then transferred into anaerobic jars containing fresh culture medium. The PA fermentations with culture medium with or without addition of arginine and aspartic acid. The PA fermentations with culture medium without addition of arginine and aspartic acid were used as control.

The culture medium: 10 g/L yeast extract, 5 g/L tryptone, 1.5 g/L $KH_2PO_4$, 2.5 g/L $K_2HPO_4$, 25 g/L glycerol, 10 mg/L $CoCl_2$, 30 g/L $CaCO_3$, 5-30 mM arginine and/or 5-30 mM aspartic acid, pH 7.0.

The method for improving PA productivity of *P. acidipropionici* by adding amino acids can be achieved through the following methods:

(1) adding 5-30 mM arginine into the culture medium;
(2) adding 5-30 mM aspartic acid into the culture medium; or
(3) adding both 5-30 mM arginine and 5-30 mM aspartic acid into the culture medium, among which the third method is preferred.

In order to obtain an optimum result, the time to add the amino acid(s) into the medium can be adjusted. For example, the amino acids can be added before fermentation, during the logarithmic growth phase, or at the stable phase. Adding the amino acids before fermentation is preferred as it is the best timing for increasing PA production.

The methods presented above significantly improved the acid tolerance and PA production of *P. acidipropionici*. The strategy mentioned above will have significant application in the large scale production of PA.

EXAMPLES

The following examples were provided by way of illustration only, and not by way of limitation.

Example 1

Improving Acid Tolerance of P. acidipropionici by Adding Arginine

The P. acidipropionici strain was stored at −80° C. in a broth containing glycerol.

To determine the effects of adding arginine on acid tolerance of P. acidipropionici, the strains were inoculated with an inoculum size of 1% (v/v) into anaerobic jars containing 100 mL sterile seed medium. The anaerobic jars were incubated at 30° C. for 60 hours. And then, the culture broth was transferred into anaerobic jars containing fresh seed medium with 2.5-5 g/L PA and 0-30 mM arginine by an inoculum size of 1% (v/v) and incubated at 30° C. for 40 hours.

Figure 1:
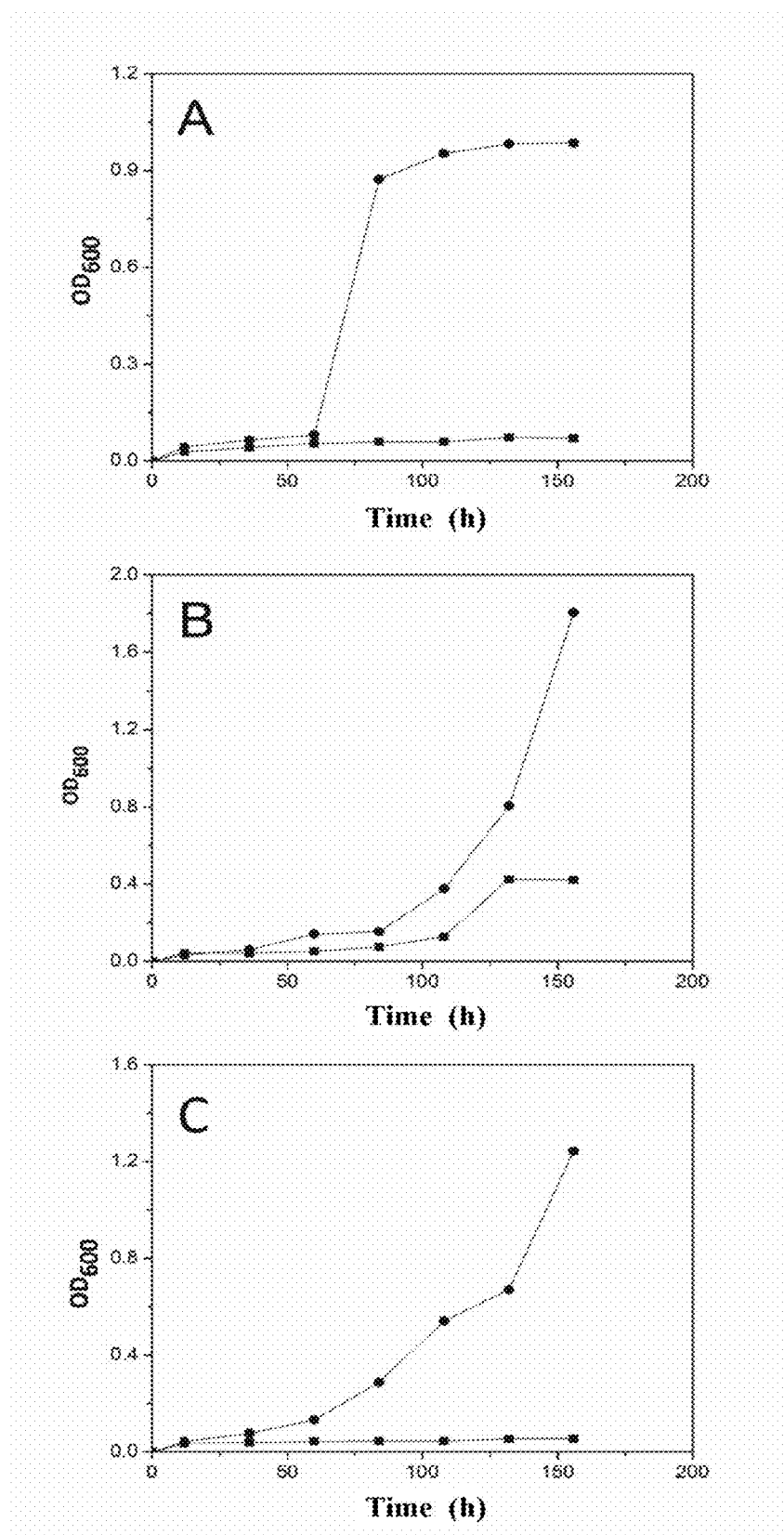
FIG. 1. Influence of amino acids addition on the acid tolerance of *P. acidipropionici*. (A) Growth curve of *P. acidipropionici* cultivated in a culture medium with or without 30 mM arginine in the presence of 4 g/L PA; (B) Growth curve of *P. acidipropionici* cultivated in a culture medium with or without 30 mM aspartic acid in the presence of 3 g/L PA; (C) Growth curve of *P. acidipropionici* cultivated in a culture medium with or without 30 mM arginine & aspartic acid in the presence of 4 g/L PA. (■, without addition of the amino acid; ●, with addition of the amino acid.)

As it can be seen from Table 1 and FIG. 1-A that P. acidipropionici was able to grow well with the medium containing 4 g/L PA and 20 mM arginine, whereas P. acidipropionici was not able to grow well with the medium containing more than 2.5 g/L PA without adding the amino acid. The result indicated that the acid concentration that P. acidipropionici can tolerate was increased by 60% with the addition of arginine.

TABLE 1

Influence of amino acid addition on the acid tolerance of P. acidipropionici

| Amino acid | amino acid concentration (mM) | Acid tolerance (g/L) |
| --- | --- | --- |
| Control | 0 | 2.5 |
| Arginine | 10 | 3 |
|  | 20 | 4 |
|  | 30 | 4 |
| Aspartic acid | 10 | 2.5 |
|  | 20 | 3 |
|  | 30 | 3 |
| Arginine and aspartic acid | 10 | 3.5 |
|  | 20 | 4 |
|  | 30 | 4 |

TABLE 2

Influence of amino acid addition on PA production of P. acidipropionici

| Amino acid | amino acid concentration (mM) | PA production (g/L) |
| --- | --- | --- |
| Control | 0 | 10.28 |
| Arginine | 10 | 10.66 |
|  | 20 | 10.60 |
|  | 30 | 13.99 |
| Aspartic acid | 10 | 12.54 |
|  | 20 | 12.97 |
|  | 30 | 12.87 |
| Arginine and Aspartic acid | 10 | 14.32 |
|  | 20 | 14.38 |
|  | 30 | 12.23 |

Example 2

Improving Acid Tolerance of P. acidipropionici by Adding Aspartic Acid

The strain was stored at −80° C. in a broth containing glycerol.

To determine the effects of adding aspartic acid on acid tolerance of P. acidipropionici, the strains were inoculated with an inoculum size of 1% (v/v) into anaerobic jars containing (volume: 100 mL) 100 mL sterile seed medium. The anaerobic jars were incubated at 30° C. for 60 hours. And then, the culture broth was transferred into anaerobic jars containing fresh seed medium with 2.5-5 g/L PA and 0-30 mM aspartic acid by an inoculum size of 1% (v/v) and incubated at 30° C. for 40 hours.

As it can be seen from Table 1 and FIG. 1 that P. acidipropionici was able to grow well with the medium containing 3 g/L PA and 20 mM aspartic acid. Without addition of aspartic acid, P. acidipropionici was able to grow only under 2.5 g/L PA. With addition of aspartic acid, P. acidipropionici was able to grow under 3 g/L PA. The result indicated that the acid concentration that P. acidipropionici can tolerate was increased by 20% with the addition of aspartic acid. As shown in Table 1, P. acidipropionici was also able to grow well with the medium containing 4 g/L PA, 20 mM arginine and 20 mM aspartic acid.

Example 3

Improving PA Production of P. acdipropionici by Adding Arginine

The strain was maintained at −80° C. in broth containing glycerol.

To determine the effects of adding arginine on PA production of P. acidipropionici, the strains were inoculated with an inoculum size of 1% (v/v) into anaerobic jars containing 100 mL sterile seed medium. And then the seed culture was inoculated with an inoculum size of 10% (v/v) into anaerobic jars (volume: 100 mL) containing 50 mL culture medium into which certain amount of arginine was added. The anaerobic jars were incubated at 30° C. for 150 h.

Figure 2:
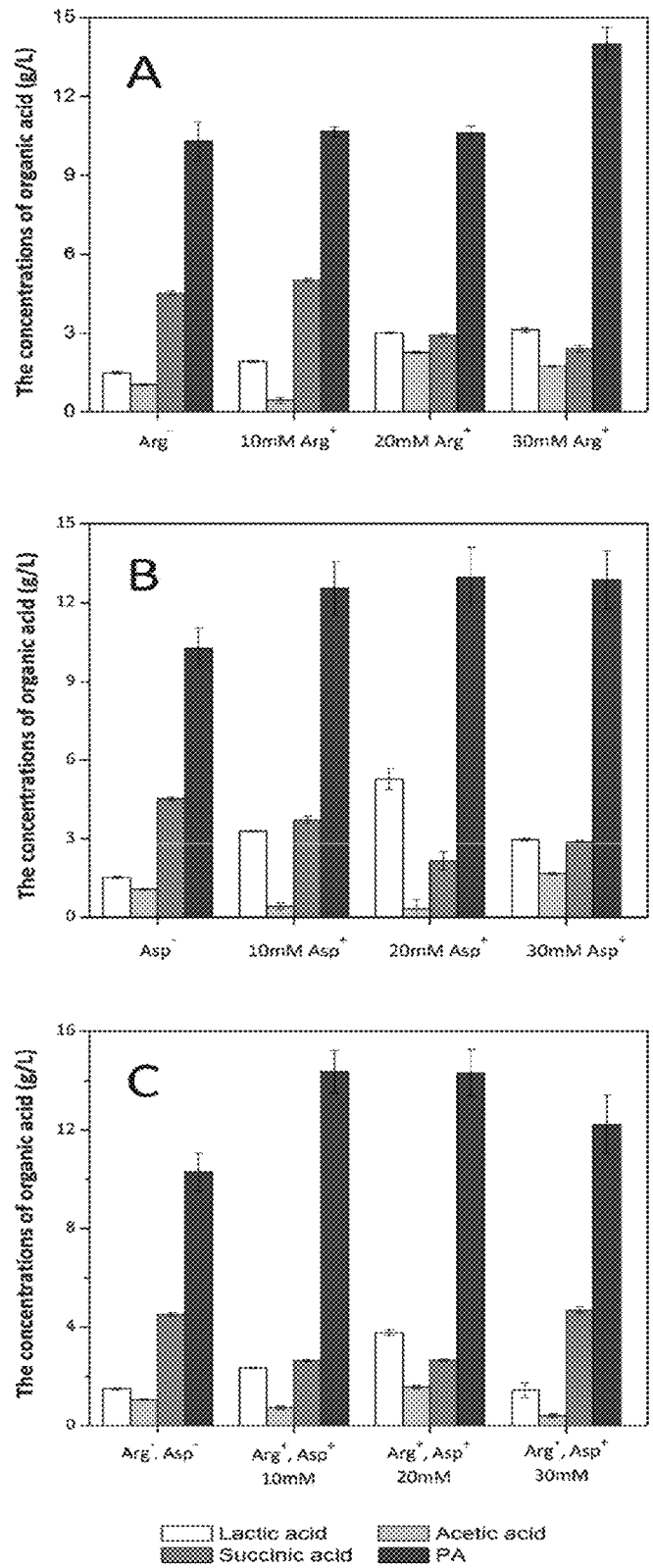
FIG. 2. Influence of amino acids addition on PA production of *P. acidipropionici*. (A) PA fermentation with addition of different concentrations of arginine: 10 mM, 20 mM, 30 mM; (B) PA fermentation with addition of different concentrations of aspartic acid: 10 mM, 20 mM, 30 mM; (C) PA fermentation with addition of different concentrations of arginine and aspartic acid: 10 mM, 20 mM, 30 mM. (Arg$^-$, without the addition of amino acids; Arg$^+$, with the addition of amino acids.)

Fermentation broth was centrifuged at 8000 rpm for 5 min, and the supernatant liquid was collected for analysis of PA. The supernatant liquid was diluted by 10 times with 3.68 mol/L sulphuric acid and then filtered with 0.22 μm pore size filter. The samples were analyzed by HPLC. As shown in Table 1 and FIG. 2, addition of amino acids increased PA production. Compared with 10.28 g/L of PA in fermentation without addition of amino acids, PA production reached 13.99 g/L with the addition of arginine.

Example 4

Improving PA Production of P. acidipropionici by Adding Aspartic Acid

The strain was stored at −80° C. in a broth containing glycerol.

To determine the effects of adding aspartic acid on PA production of P. acidipropionici, the strains were inoculated with an inoculum size of 1% (v/v) into anaerobic jars containing 100 mL sterile seed medium. And then the seed culture was inoculated with an inoculum size of 10% (v/v) into anaerobic jars (volume: 100 mL) containing 50 mL culture medium into which certain amount of aspartic acid was added. The anaerobic jars were incubated at 30° C. for 150 hours.

Fermentation broth was centrifuged at 8000 rpm for 5 min, and the supernatant liquid was collected for analysis of PA. The supernatant liquid was diluted by 10 times with 3.68 mol/L sulphuric acid and then filtered with 0.22 μm pore size filter. The samples were analyzed by HPLC. As shown in Table 2 and FIG. 2, addition of amino acids increased PA production. Compared with 10.28 g/L of PA in fermentation without addition of amino acids, PA production reached 12.97 g/L with the addition of aspartic acid. With the addition of 20 mM arginine and aspartic acid, the maximal PA titer reached 14.38 g/L, increased by 39.9%.

Example 5

Improving PA Production of *P. acidipropionici* by Adding Amino Acids in the Logarithmic Phase 12.60 g/L and 12.75 g/L PA were obtained by adding 30 mM arginine and 20 mM aspartic acid, respectively, at the logarithmic phase of fermentation process. With the addition of both 20 mM arginine and 20 mM aspartic acid, PA production was further increased to 13.62 g/L.

Example 6

Improving PA Production of *P. acidipropionici* by Adding Amino Acids in the Stable Phase 10.65 g/L and 10.66 g/L PA were obtained by adding 30 mM arginine and 20 mM aspartic acid, respectively, at the stable phase of fermentation process. With the addition of both 20 mM arginine and 20 mM aspartic acid, PA production was further increased to 11.36 g/L.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for improving acid tolerance of *P. acidipropionici* comprises adding arginine into a culture medium during culturing said *P. acidipropionici*.

2. The method of claim 1, wherein said arginine is added with a concentration of 5-30 mM.

3. The method of claim 2, wherein said arginine is added with a concentration of 30 mM.

4. The method of claim 2, further comprising adding 5-30 mM aspartic acid into the culture medium.

5. The method of claim 4, wherein said arginine and aspartic acid are both added at concentrations of 10-30 mM each.

6. The method of claim 5, wherein said concentrations of said arginine and aspartic acid are both 20 mM.

7. The method of claim 4, wherein said arginine and said aspartic acid are added into the culture medium before the beginning of culturing said *P. acidipropionici*.

8. The method of claim 2, further comprising adding 30 mM aspartic acid into the culture medium.

9. The method of claim 1, wherein said arginine is added into the culture medium before the beginning of culturing said *P. acidipropionici*.

10. A method for improving the production of propionic acid of *P. acidipropionici* comprises adding arginine into a culture medium during culturing said *P. acidipropionici*.

11. The method of claim 10, wherein said arginine is added with a concentration of 5-30 mM.

12. The method of claim 11, wherein said arginine is added with a concentration of 30 mM.

13. The method of claim 10, further comprising adding 5-30 mM aspartic acid into the culture medium.

14. The method of claim 13, wherein said arginine and aspartic acid are both added at concentrations of 5-30 mM each.

15. The method of claim 14, wherein said concentrations of said arginine and aspartic acid are both 20 mM.

16. The method of claim 13, wherein said arginine and said aspartic acid are added into the culture medium before the beginning of culturing said *P. acidipropionici*.

17. The method of claim 10, further comprising adding 30 mM aspartic acid into the culture medium.

18. The method of claim 10, wherein said arginine is added into the culture medium before the beginning of culturing said *P. acidipropionici*.

* * * * *